(12) United States Patent
Wallace et al.

(10) Patent No.: US 6,432,128 B1
(45) Date of Patent: *Aug. 13, 2002

(54) INTRACRANIAL STENT AND METHOD OF USE

(75) Inventors: George Wallace; Jay Lenker; Thomas J. Berryman, all of San Clemente, CA (US)

(73) Assignee: Micro Therapeutics, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/474,050

(22) Filed: Dec. 28, 1999

Related U.S. Application Data

(62) Division of application No. 08/707,996, filed on Sep. 18, 1996, now Pat. No. 6,007,573.

(51) Int. Cl.[7] ................................................. A61F 2/06
(52) U.S. Cl. ..................................... 623/1.11; 606/198
(58) Field of Search ............................ 623/1.15, 1.11; 606/198, 191, 194, 195

(56) References Cited

U.S. PATENT DOCUMENTS

| | | | |
|---|---|---|---|
| 4,740,207 A | 4/1988 | Kreamer | 623/1 |
| 4,776,337 A | 10/1988 | Palmaz | 606/194 |
| 4,830,003 A | 5/1989 | Wolff et al. | 128/343 |
| 4,923,464 A | 5/1990 | DiPisa | 606/195 |
| 4,969,890 A | 11/1990 | Sugita et al. | 606/192 |
| 5,007,926 A | 4/1991 | Derbyshire | 623/1 |
| 5,100,429 A | 3/1992 | Sinofsky et al. | 606/195 |
| 5,139,480 A | 8/1992 | Hickle et al. | 606/191 |
| 5,211,654 A | 5/1993 | Kaltenbach | 606/191 |
| 5,306,294 A | * 4/1994 | Winston et al. | 623/1.15 |
| 5,354,309 A | 10/1994 | Schnepp-Pesch et al. | 606/198 |
| 5,405,379 A | 4/1995 | Lane | 623/1 |
| 5,411,549 A | 5/1995 | Peters | 606/194 |
| 5,411,551 A | * 5/1995 | Winston et al. | 623/1.15 |
| 5,441,515 A | 8/1995 | Khosravi | 606/194 |
| 5,443,458 A | 8/1995 | Eury | 606/198 |
| 5,443,500 A | 8/1995 | Sigwart | 623/1 |
| 5,449,373 A | 9/1995 | Pinchasik et al. | 606/198 |
| 5,545,210 A | 8/1996 | Hess | 623/1 |
| 5,603,722 A | * 2/1997 | Phan et al. | 606/198 |
| 5,637,113 A | 6/1997 | Tartaglia et al. | 623/1 |
| 5,676,697 A | 10/1997 | McDonald | 623/1 |
| 5,707,387 A | 1/1998 | Wijay | 606/194 |
| 5,728,150 A | 3/1998 | McDonald et al. | 623/1 |
| 5,766,710 A | 6/1998 | Turnland et al. | 623/1 |

FOREIGN PATENT DOCUMENTS

| | | | |
|---|---|---|---|
| EP | 0709067 A2 | 1/1996 | A61F/2/06 |
| WO | 9404096 | 3/1994 | 623/1 |
| WO | 9421196 | 9/1994 | 623/1 |

OTHER PUBLICATIONS

Marks, et al., Stent Placement for Arterial and Venous Cerebrovascular Disease, 191 Radiology 441 (1994).

Eskridge, Neurovascular Stents, 191 Radiology 313 (1994).

(List continued on next page.)

Primary Examiner—Kevin T. Truong
(74) Attorney, Agent, or Firm—K. David Crockett, Esq.; Crockett & Crockett

(57) ABSTRACT

A stent and stent catheter for intra-cranial use. The stent is a rolled sheet stent and is releasably mounted on the distal tip of the catheter with a low profile retaining tab. The stent is rolled tightly on the distal tip of the catheter and flexibility of the tightly rolled stent is promoted by ribbed or slatted construction (or, alternatively, slotted construction) in which the various layers of the stent are provided with numerous slats which counter align when the stent is expanded to form an imperforate wall from a plurality of perforate layers.

4 Claims, 10 Drawing Sheets

OTHER PUBLICATIONS

Becker, Should Metallic intravascular Stents Be Used to Treat Cerebrovascular Occlusive Diseases, 191 Radiology 309 (1994).

Hull, The Wallstent In Peripheral Vascular Disease: For Iliac Use Only, 6 JVIR 841 (Nov.–Dec. 1995).

Szikora, et al., Combined Use Of Stents And Coils To Treat Experimental Wide–Necked Carotid Aneurysms, 15 AJNR 1091 (Jun. 1994).

Zollikofer, Historical Overview On The Development And Characteristics Of Stents And Future Outlooks, 15 Cardiovasc. Intervent. Radiol. 272 (1992).

Civit, et al., Aneurysm Clipping After Endovascular Treatment With Coils, 38 Neurosurgery 955 (May 1996).

Wakhloo, et al., Self–Expanding Nitinol Stents in Canine Vertebral Arteries, 16 AJNR 1043 (May 1995).

Geremia, et al, Embolization of Experimentally Created aneurysms with Intravascular Stent devices, 15 AJNR 1223 (Aug. 1994).

Berry, et al., *A Method To Evaluate The Elastic Behavior Of Vascular Stents*, 7 J Vasc. Interv. Radiol. 381–5 (May–Jun. 1996).

Palmaz, *Intravascular Stents: Tissue–Stent Interactions and Design Considerations*, 160 Am. J. Rad. 613 (Mar. 1993).

Abbott, et al., *Effect Of Compliances Mismatch On Vascular Graft Patency*, 5 J. Vasc. Surg. 376 (1987).

Palmaz, Intravascular Stenting, 15 Cardiovasc. Interv. Rad. 279 (1992).

\* cited by examiner

INTRACRANIAL STENT AND METHOD OF USE

This application is a divisional of U.S. app. Ser. No. 08/707,996, filed Sep. 18, 1996, now U.S. Pat. No. 6,007,573.

FIELD OF THE INVENTION

This invention relates to treatments for vascular disease.

BACKGROUND OF THE INVENTION

The inventions described below were developed with the goal of providing new and better therapies for certain types of vascular disease for which the present day therapies are widely regarded as inadequate. Vascular disease includes aneurysms which can rupture and cause hemorrhage, atherosclerosis which can cause the occlusion of the blood vessels, vascular malformation and tumors. Occlusion of the coronary arteries, for example, is a common cause of heart attack. Vessel occlusion or rupture of an aneurysm within the brain are causes of stroke. Tumors fed by intra-cranial arteries can grow within the brain to the point where they cause a mass effect. The mass and size of the tumor can cause a stroke or the symptoms of stroke, requiring surgery for removal of the tumor or other remedial intervention.

Other therapies for occlusions of various arteries are under development. Balloon angioplasty is a technique in which a balloon is inserted into a stenosis which occludes or partially occludes an artery and is inflated in order to open the artery. Atherectomy is a technique in which occlusive atheromas are cut from the inner surface of the arteries. The newly preferred therapy for coronary occlusions is placement of an expanded metal wire-frame, called a stent, within the occluded region of the blood vessel to hold it open. Stents of various construction have been proposed, including the Palmaz-Schatz™ balloon expandable metal stent, the Wallstent self-expanding braided metal stent, the Strecker knitted metal stent, the Instent™ coil stent, the Cragg coiled stent and the Gianturco Z stent. Stents have been proposed for treatment of atherosclerosis in the neck, but carotid endarterectomy is still the preferred treatment for stenosis. Most perioperative strokes are thought to be caused by technical errors during endarterectomy (see Becker, Should Metallic Vascular Stents Be Used To Treat Cerebrovascular Occlusive Disease, 191 Radiology 309 (1994)). The same concerns militate against other forms of therapy such as angioplasty for treatment of the carotid arteries. Various factors, including poor long-term patency, distal emboli causing a stroke, the potential for crushing from external pressure, and the need for long term anti-coagulation, lead to the avoidance of certain stents in vessels smaller than the iliac arteries or in locations susceptible to external pressure. See, for example, Hull, The Wallstent in Peripheral Vascular Disease, For Iliac Use Only, 6 JVIR 884 (November–December 1995).

Stent grafts have been proposed and used to treat aneurysms in the large blood vessels such as the aorta, and these typically include tube graft material supported by a metallic stent. These stent grafts are designed for use in the large blood vessels, and the various layers of stents and grafts make them unsuitable for use in smaller blood vessels. Stent grafts are not currently used in the coronary arteries which are typically 3 or 4 mm in internal diameter. Rolled stents have been proposed for use in aortic aneurysms. For example, Lane, Self Expanding Vascular Endoprosthesis for Aneurysms, U.S. Pat. No. 5,405,379 (Apr. 11, 1995) suggests the use of a polypropylene sheet placed in the abdominal or thoracic aorta to bridge aneurysms. It is particularly emphasized in Lane that the rolled sheet must be imperforate. Winston, Stent Construction of Rolled Configuration, U.S. Pat. No. 5,306,294 (Apr. 26, 1994) proposes a rolled sheet of stainless steel. Neither device is believed to have been used or approved for use in humans. Of similar construction are the single layer rolled stents such as Kreamer, Intraluminal Graft, U.S. Pat. No. 4,740,207 (Apr. 26, 1988) and its reissue Re 34,327 (Jul. 27, 1993), which are expanded by balloon and include a ratchet mechanism which projects into the lumen of the stent, thus making it unsuitable for critical vessels in the brain and small diameter vessels. Khosravi, Ratcheting Stent, U.S. Pat. No. 5,441,155 (Aug. 15, 1995) and Sigwart, Intravascular Stent, U.S. Pat. No. 5,443,500 (Aug. 22, 1995) are other examples of rolled stents with ratcheting locking mechanisms.

Aneurysms of peripheral arteries and arteries of the neck have been treated experimentally with open walled stents such as the Strecker braided stent. Szikora, et al., Combined use of Stents and Coils to treat Experimental Wide-Necked Carotid Aneurysms, 15 AJNR 1091 (June 1994) illustrates use of a Strecker stent in the proximal vertebral arteries in dogs, and teaches that an open walled or porous stent is required to avoid excessive ingrowth. The Strecker stent has a very small metal to blood vessel surface ratio, and has large openings between each of the wires making up the stent. The current technique in the use of open walled stents in the aneurysms of peripheral arteries is based on the theory that placement of the open walled stent slows the blood flow in the aneurysmal sac, leading eventually to the formation of clots and fibrous masses which occlude the aneurysm. This technique has been combined with placement of micro-coils through the wall of the stent and into the aneurysm to further encourage fibrous tissue development within the aneurysm. The Szikora article and others show that knitted stents have not been effective in isolating an aneurysm from the circulatory system. Another problem noted with this technique is that blood clots can escape the open walled stent.

Stents have not previously been used for aneurysms of the blood vessels in the brain. The vessels in the brain likely to develop stenosis, aneurysms, AVM's and side branches requiring occlusion have diameters of about 1 mm to 5 mm, and can be accessed only via highly tortuous routes through the vascular system. Instead, clipping, resection, complete occlusion with acrylic-based adhesives (super glue) or small balloons (thereby intentionally occluding the downstream portion of the blood vessel and any portion of the brain supplied by that portion), stuffing with foreign objects, etc. have been used. In a method of current interest, small coils are stuffed into the aneurysm via a catheter. One such small coil is known as the Guglielmi Detachable Coil or GDC. After placement of a few coils, which partially obstruct blood flow in the aneurysm, the blood clots or fibrous matter forms within the sac. This technique has reportedly resulted in clots and coils falling out of the sac, and the technique is not used on wide-neck aneurysms. Aneurysm clipping, in which the skull is opened and the brain dissected to expose the outside of the aneurysm, followed by placement of clips at the base of the aneurysm, is also an option for treatment. However, these techniques do not always effect an immediate and complete seal of the aneurysm from the high pressure of the circulatory system, and rupture, leakage and deadly complications occur. Aneurysm rupture and bleeding during surgical clipping and shortly after the clip placement is a significant problem and add difficulty to the procedure. Examples of the problems inherent in the use of both GDC's and aneurysm clips are illustrated in Civit, et al., Aneurysm Clipping After Endovascular Treatment With Coils, 38 Neurosurgery 955 (May 1996) which reports that several patients in the study died after unsuccessful coil placement and before they could be re-treated with the open skull clip placement. Thus the article illustrates that GDC's do not always work, and when they fail they may leave the patient in a critical condition. As illustrated in the article, bleeding during surgical clipping and shortly after the clip placement is also a frequent problem.

From experiences like this, it is apparent that the ultimate goal of intracranial aneurysm treatment is the complete or nearly complete exclusion of the aneurysm cavity from the circulation, which prevents bleeding into the brain cavity and prevents formation of distal blood clots. This goal may be achieved immediately to ensure successful treatment by means of a substantially imperforate stent. It may also be achieved with a slightly perforated stent which alters flow in such a way that compete clotting, over time, is initiated within the aneurysm. It may also be achieved with a perforate stent through which embolic material such as coils are placed in the aneurysm. The treatments may be accomplished by placement of the stents described below which generally do not require the use of balloons for expansion of the stent, so that the blood vessel being treated is not occluded during placement of the stent.

SUMMARY OF THE INVENTION

Stents for intra-cranial use and methods for using these stents are described in detail below. The physical characteristics of prior art balloon expandable stents and self expanding stents make them clearly unsuitable for intra-cranial use, because of their delivery profile and tendency to temporarily occlude the vessel during deployment. They have not been proposed for intra-cranial use. Palmaz stents, Palmaz-Schatz™ stents, Wallstents, Cragg stents, Strecker stents and Gianturco stents and other stents are too rigid to allow placement in the cerebral blood vessels, some require a balloon for deployment, and all are too open to occlude an aneurysm. Presented below are several embodiments of stents suitable for intra-cranial use, along with methods for using these stents to treat intra-cranial vascular disease.

The self expanding rolled sheet stent is suitable for use in the intra-cranial arteries. The rolled sheet is made of Elgiloy™, nitinol, stainless steel, plastic or other suitable material, and is imparted with resilience to urge outward expansion of the roll to bring the rolled stent into contact with the inner wall of a diseased artery. The rolled sheet is adapted for easy insertion and non-deforming radial flexibility to facilitate tracking along the tortuous insertion pathways into the brain. In some embodiments, as much of the material of the stent is removed as is consistent with eventual creation of a solid walled stent upon unrolling of the stent within the blood vessel. The unrolled stent may be two or more layers of Elgiloy™, thus providing radial strength for the stent and creating at least a slight compliance mismatch between the stent and the blood vessel, thereby creating a seal between the stent and the blood vessel wall. For placement, the stent is tightly rolled upon or captured within the distal tip of an insertion catheter. The release mechanism is extremely low profile, and permits holding the rolled stent in a tight roll during insertion and permits atraumatic release when in the proximity of the site of arterial disease, without occluding the vessel with the deployment catheter. The stent can be placed in the intra-cranial blood vessels (arteries and veins) of a patient to accomplish immediate and complete isolation of an aneurysm and side branches from the circulatory system. The stent may be placed across a target site such as an aneurysm neck, origin of a fistula, or branch blood vessels feeding a tumor in order to redirect the flow of blood away from the target. It can be used as a stand alone device which is left in the intra-cranial artery permanently, or it may be used as a temporary device which allows for immediate stabilization of a patient undergoing rupture of a blood vessel aneurysm or awaiting open skull surgery for clipping or resection of an aneurysm. The stent can be used for stabilization and isolation of a vascular defect during surgery of the vascular defect. Another advantage of this type of stent is that it can be wound down should repositioning be required prior to full release. It is possible to rewind and reposition or remove the device using grasping tools.

DETAILED DESCRIPTION OF THE INVENTION

Figure 1:
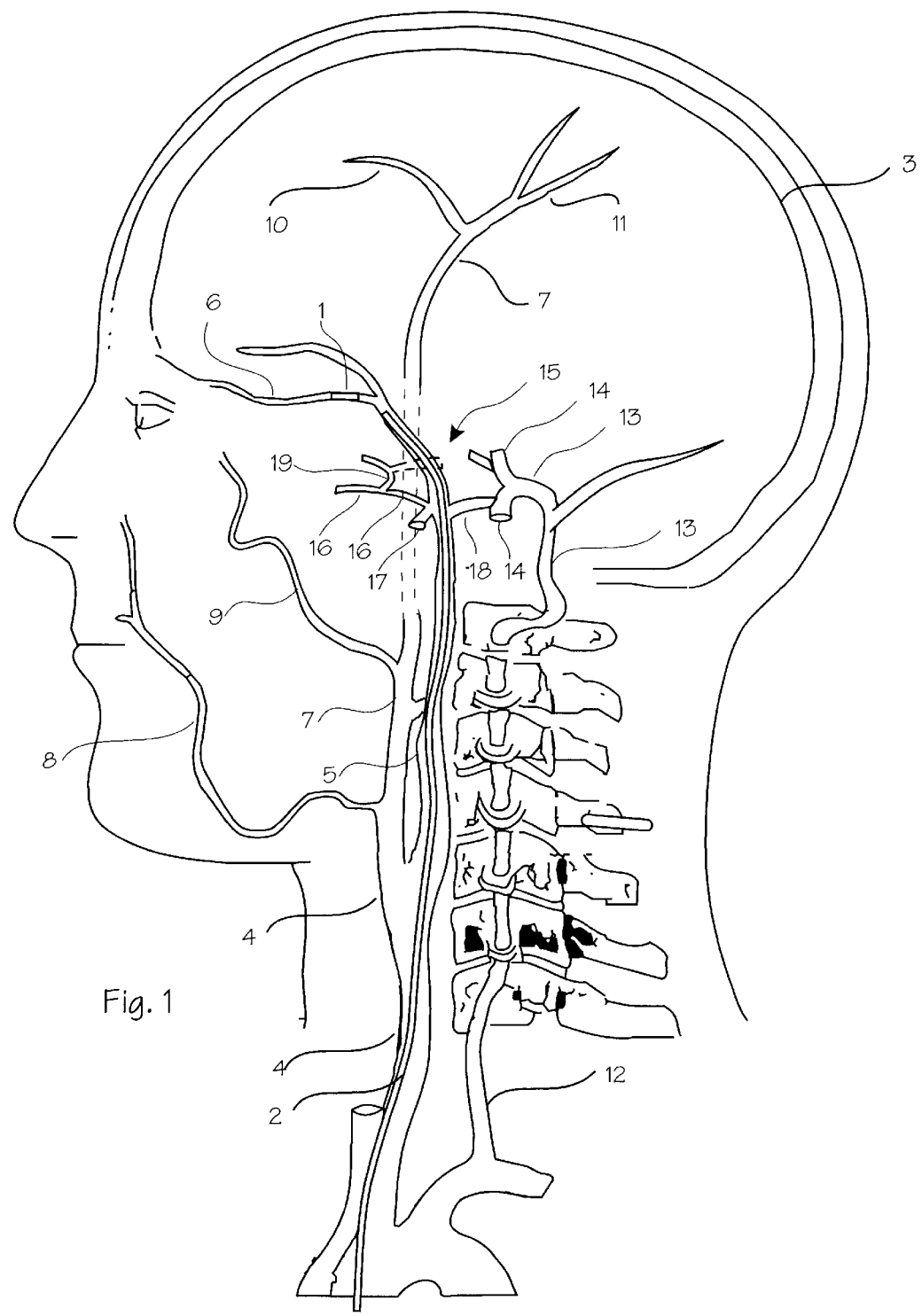
FIG. 1 is a schematic diagram of the vasculature of the brain showing a typical placement of an intra-cranial stent.
Figure 2:
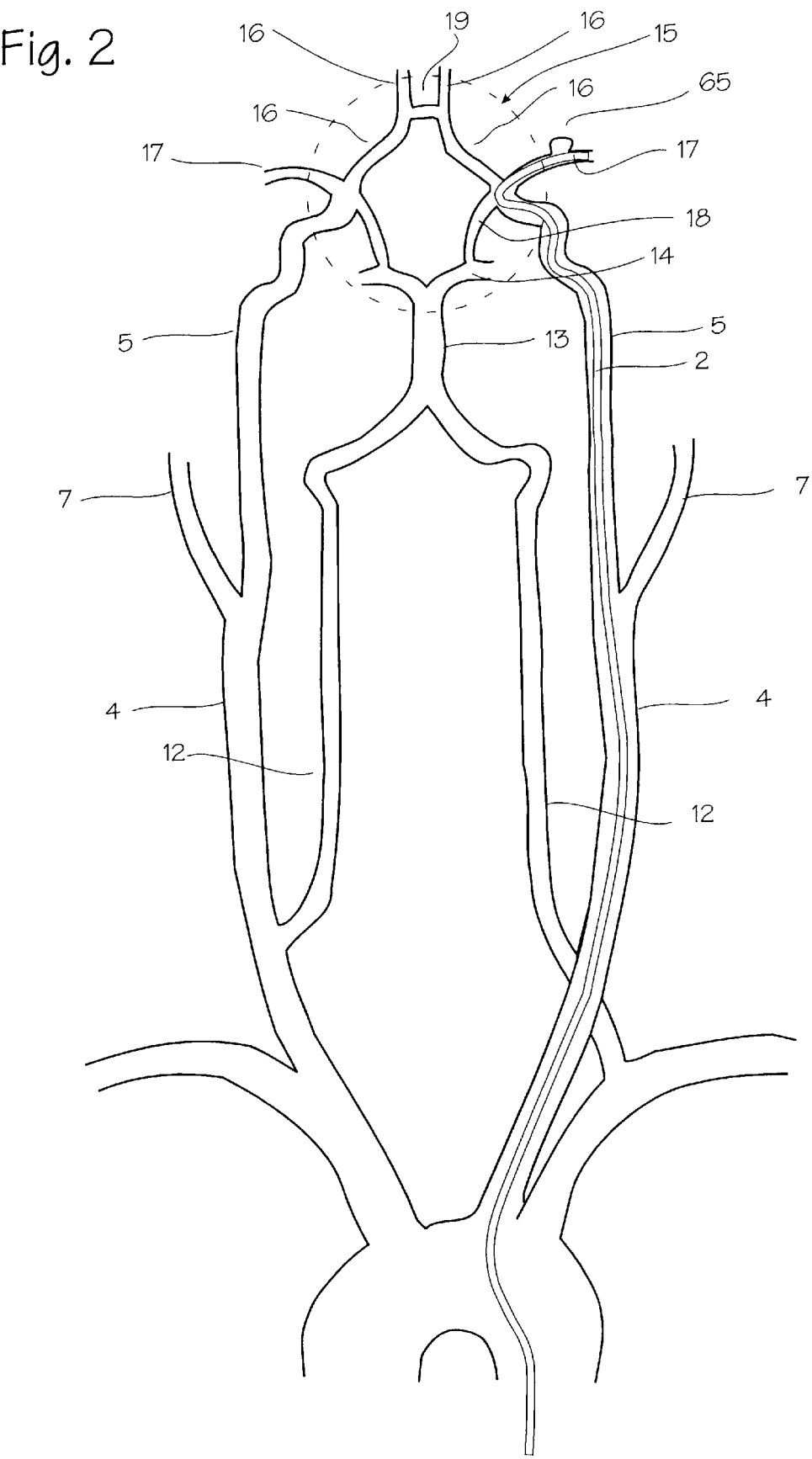
FIG. 2 is schematic diagram of the vascular of the brain illustrating the circle of Willis and arteries supplying the circle of Willis.

FIGS. 1 and 2 show the vasculature of the brain in sufficient detail to understand the invention. The brain 3 is supplied with blood through the carotid and the vertebral arteries on each side of the neck. The important arteries include the common carotid artery 4 in the neck, which will be the most common access pathway for the stent, the internal carotid 5 which supplies the opthalmic artery 6. The external carotid 7 supplies the maxillary artery 8, the middle meningeal artery 9, and the superficial temporal arteries 10 (frontal) and 11 (parietal). The vertebral artery 12 supplies the basilar artery 13 and the cerebral arteries including the posterior cerebral artery 14 and the circle of Willis indicated generally at 15. Also supplied by the internal carotid artery are the anterior cerebral artery 16 and the middle cerebral artery 17, as well as the circle of Willis, including the posterior communicating artery 18 and the anterior communicating artery 19. These arteries typically have an internal diameter of about 1 mm to 5 mm, most commonly from 2–4 mm. The methods and devices described herein allow access to these arteries and placement of a stent in these arteries. In FIG. 1, the insertion catheter 2 and stent 1 are shown threaded through the common carotid artery 4 and the internal carotid artery 5, with the stent extending into the anterior cerebral artery 16.

FIG. 2 shows the same blood vessels in a schematic view that better illustrates the circle of Willis and the arteries which supply this important anatomic feature. The circle of Willis 15 is a ring of arteries connecting the internal carotid arteries and the basilar artery (and hence the left and right vertebral arteries) to the anterior cerebral arteries 16, middle cerebral arteries 17 and posterior cerebral arteries 14. The system provides a redundant supply of blood to the cerebral arteries. Aneurysms, fistulas, AVM's and tumors occurring inside the brain, in the intracranial portion of the carotid arteries, vertebral arteries and basilar artery, in the circle of Willis or even deeper within the brain may be treated with the stents and delivery systems described below. FIG. 2 shows an exemplary use in which a delivery catheter 2 is inserted through the aorta into the common carotid, internal carotid and through the circle of Willis 15 into the middle cerebral artery 17 to treat an aneurysm 65 with a stent which is held on or within the distal tip of the delivery catheter.

Figure 3:
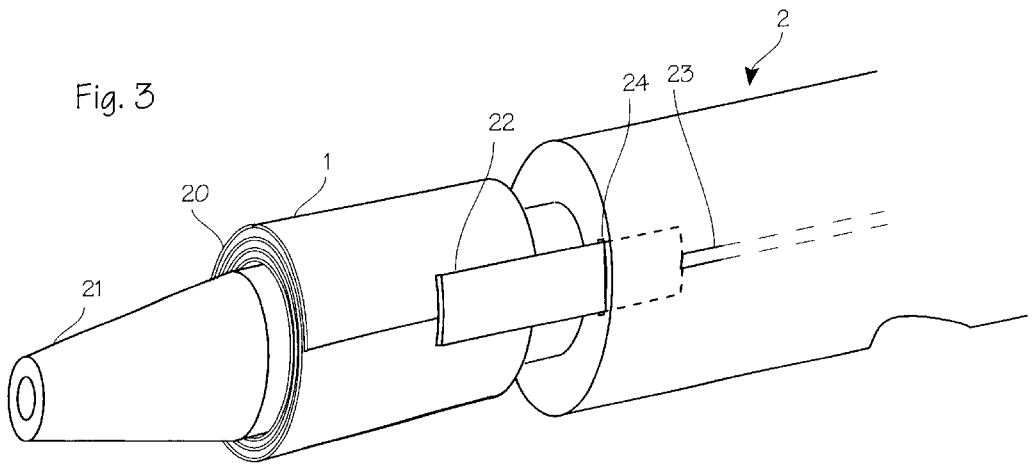
FIG. 3 is an elevational view of the rolled stent mounted on an insertion catheter.

FIG. 3 shows the overall structure of the stent 1, when mounted in the delivery catheter 2. The stent 1 is comprised of a single sheet 20 of Elgiloy™, stainless steel, nitinol, plastic or other suitable material. The metals are processed so as to provide a high level of spring property. Such processing includes cold rolling and suitable heat treatment. The stent is rolled tightly around the insertion catheter distal tip 21. Retaining clip 22 holds the sheet in a tight roll around the catheter. The retaining clip or tab is operated by pull wire 23 which extends out the proximal end of the catheter. The retaining tab is slidably disposed within the arcuate side lumen 24 and extends distally from the side lumen to hold the stent in a tight roll on the distal tip of the catheter. The retaining clip or tab 22 is operably connected to the proximal end of the catheter via a pullwire so that the retaining tab may be pulled proximally into the arcuate side lumen to release the stent. The clip mechanism provides for a lower profile than the construction of other stents such as the Winston stent and the Lane stent which require spools or sheaths. In another embodiment, an electrolytic charge may be used to release a securing attachment to the stent, thus allowing for stent expansion and/or release from the catheter. The clip may be made of tantalum or other radiopaque material so that it is clearly visible under fluoroscopy. The outer diameter of the stent, when rolled tightly around the distal tip of the catheter, will typically be 1–3 French (0.3 mm to 1 mm), and may be as small as 1 French, about 0.3 mm (0.012 inches or 12 mil), or even smaller. The stent may also be coated with radio-dense material (tin, tantalum, etc.) to enhance visibility under fluoroscopy. Also, radiopaque markers of tantalum, platinum or gold may be attached to the stent.

Figure 4:
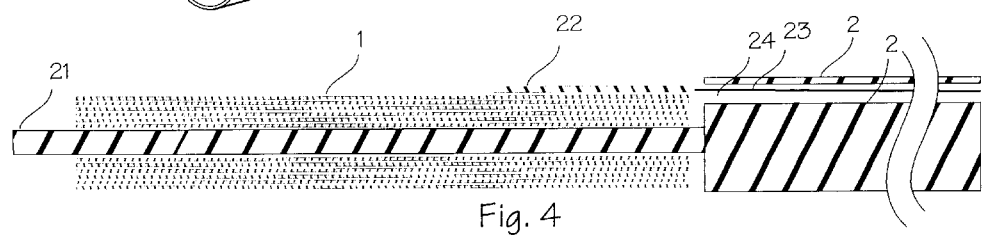
FIG. 4 is a cross section of a preferred embodiment of the stent catheter.

FIG. 4 shows the cross section of the insertion catheter 2 with the stent 1 mounted and retained by the retaining clip 22. The retaining clip has a circumferential radius matching the outer diameter of the rolled stent, and may be pulled by pullwire 23 into the arcuate side lumen of the insertion catheter. Upon pull-back of the retaining clip, the stent will release and unroll or unwind to a diameter of about 1 mm or less, or as much as 5 or 6 mm. After release, the stent will have at least one layer in the unwound state. A single layer may partially cover the interior surface of the blood vessel wall (see FIGS. 19 and 20), may completely cover the surface with a single layer of stent material, or may cover the interior surface with more than one layer of stent material. Use of multiple layers provides extra columnar and radial strength (i.e., resistance to compression or resistance to unwinding or re-rolling in response to compressive forces) vis-à-vis a single layer, and this extra strength is beneficial in view of the modifications of the stent as described below to enhance the radial and longitudinal flexibility of the stent. Another embodiment allows for a single layer stent across the vessel anomaly to be occluded and one or more layers at the stent vessel anastomosis site (the endpoints of the stent).

Figure 5:
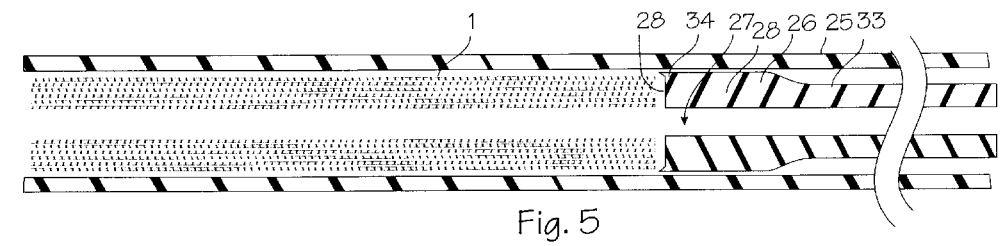
FIG. 5 is a cross section of a second preferred embodiment of the stent catheter.
Figure 6:
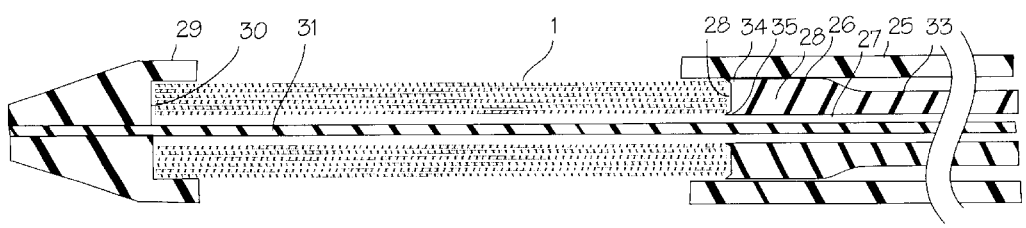
FIG. 6 is a cross section of a third preferred embodiment of the stent catheter.

FIG. 5 shows a cross section of the stent 1 mounted in an insertion catheter sheath 25. The stent is tightly rolled within the distal tip of the catheter sheath and it is delivered to the target site within the distal tip of the delivery sheath. A push rod 26 with an optional central lumen 27 and a distal face 28 abuts the proximal end of the rolled stent. In order to insert the stent within the blood vessel, the push rod 26 is used to hold the stent in place while the catheter sheath is retracted proximally to uncover the stent, or it is used to push the stent out from the sheath. Once the stent is free of the catheter sheath, it will unroll until it meets the inner wall of the blood vessel. FIG. 6 shows a cross section of a delivery catheter which provides both distal and proximal release mechanisms. The stent 1 is trapped between the push rod 26 and the distal retainer 29. The receiving bore 30 of the retainer 29 closely matches the outer diameter of the rolled stent. The internal diameter of the catheter sheath 25 also closely matches the outer diameter of the rolled stent. The external diameter of the delivery catheter is only slightly larger than the outer diameter of the tightly rolled stent. The stent is rolled tightly and trapped within the bore of the distal retainer. The distal retainer is controlled by control rod 31 which extends the length of the catheter and passes through the central lumen of the push rod 26. Preferably, the retainer control rod has an outer diameter significantly smaller than the inside diameter of the tightly rolled stent, so that it does not interfere with flexing of the stent during deployment. The retainer control rod may instead have an outer diameter equal to the inner diameter of the rolled stent, so that the stent is directly rolled around the control rod and the control rod functions as a spool or core to support the rolled stent. This delivery catheter is operated by releasing either the proximal or distal end of the stent through appropriate movement of the distal retainer, the push rod, or the catheter sheath. The stent may be released distal end first by pushing the retainer control rod in the distal direction to release the stent, or it may be released proximal end first by pushing the pushing rod forward and distally out from the catheter sheath or withdrawing the catheter sheath in the proximal direction to release the proximal end of the stent. The need for proximal-end-first or distal-end-first release will be determined during surgery, and will be accomplished as medically indicated.

The push rod 26 must fit within the catheter sheath with very close tolerances to ensure that the rolled stent is uniformly pushed from the catheter sheath and the outer roll of the stent cannot get caught between the push rod and the catheter sheath. Thus, the distal tip 32 of the push rod is enlarged relative to the proximal portion 33 of the push rod so that the distal face of the push rod has a diameter which closely matches the inner diameter of the catheter sheath. The distal face 28 of the push rod is provided with a beveled rim 34 around the outer circumference the distal face to force the stent to preferentially slip toward the center of the distal face and away from possibly interfering positions between the push rod and the catheter sheath. A beveled rim 35 may be applied also to the inside bore of the push rod (FIG. 6) to prevent the inner roll of the stent from slipping into the push rod center lumen and getting caught between the push rod and the distal retainer control rod. FIGS. 4, 5 and 6 thus illustrate means of securing the stent to the distal end of a catheter and retaining the stent in the tightly rolled configuration during insertion, and two means of inserting the stent into the blood vessel. Other means for retaining the stent include rings, pull-strings, string wraps, bars, and a catheter sleeve and electrolytic fusible joint or fusible link.

The stent may be a simple rolled sheet of Elgiloy™, nitinol, stainless steel or other resilient material. Elgiloy™ is preferred because it is less likely for the inner layer of the tightly rolled stent to take a set or become creased or crimped, which may occur in a stainless steel roll when the inner layer of the stent is tightly rolled in its deployment configuration. Plastics, bioabsorbable materials, and other materials may also be beneficially used. Polyesters, polypropylene, polyethylene, polylactic acid and polyglycolic acid are contemplated alternative materials for the stent.

Figure 7:
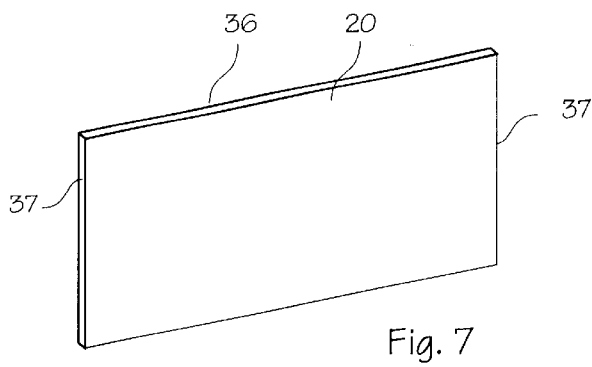
FIG. 7 is a view of a simple embodiment of the stent.

The basic embodiment comprises a sheet of Elgiloy™ about 0.0025 to 0.025 mm thick (0.1 mils to 1 mil, or 0.0001 to 0.0010 inches). Referring to FIG. 7, the wrap length represented by transverse edge 36 will be about 6–75 mm, allowing the stent to expand to diameters from about 1 mm to about 6 mm with approximately two to three layers after expansion. The bridge length represented by axial edge 37 (or the longitudinal edge) will vary according to the width of the aneurysm which must be isolated with the stent, and may vary from 2 to 20 mm, for example. The stent is tempered or formed so that it resiliently unrolls and expands to a diameter of approximately 1 mm to 6 mm, and provides a slight compliance mismatch with the intra-cranial arteries which have internal diameters of about 1 mm to 6 mm. When expanded, the stent intended for most intracranial applications will comprise a tube of one to three rolled layers. The stents described above can provide expansion ratios of five to one or greater. Expansion ratios of less than five to one may be achieved if desired. For particular intracranial applications, stents having more than three layers may be used. Stents comprising less than a single layer when unrolled will also be useful, as illustrated below in reference to FIG. 18.

Figure 8:
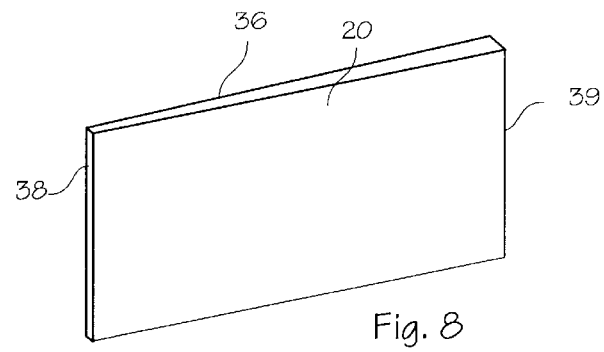
FIG. 8 is a view of a preferred embodiment of the stent.
Figure 14:
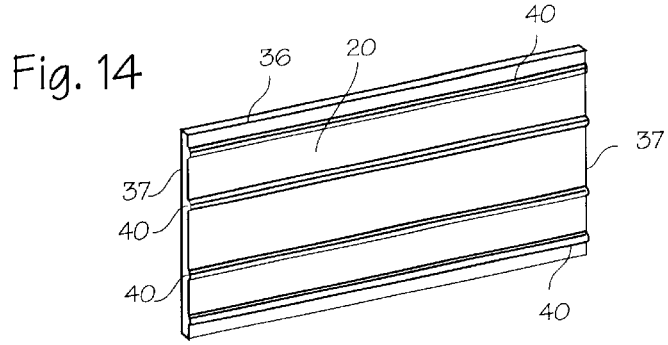
FIG. 14 is a view of an alternative embodiment of the stent.

The stent will be more flexible, and easier to bend around the various twists and turns of the blood vessels, if modified according to FIGS. 8 through 12. The stent may have a thickness which gradually increases along the transverse edge, as shown in FIG. 8. When the stent is expanded, the material of the inner layers is thinner than the outer layers. Thus, the inner edge 38 is thinner than the outer edge 39. This construction permits the stent to flex sideways even when rolled tightly to the distal tip of the insertion catheter and mitigates the tendency of the innermost edge of the stent to be permanently deformed in its rolled down state. The inner edge may be as small as 0.0025 mm (0.1 mil), and the thickness can gradually thicken to 0.05 mm (2 mils) at the outer edge. In FIG. 14, the stent is modified with the provision of ribs 40 that extend transversely across the width of the rolled sheet, or at a slight angle to the transverse edge. The wall thickness in the interstitial portions between the ribs may be quite thin, less than 0.0025 mm (0.1 mil), and yet the stent has sufficient resilience to expand into its open configuration and exert pressure against the inner wall of a small blood vessel. This property will allow the stent to remain in position and maximize the sealing characteristics of the device. The ribs may be applied only at the distal and proximal ends of the stent, and may be integrally formed as gradually increasing stent thickness.

Figure 9:
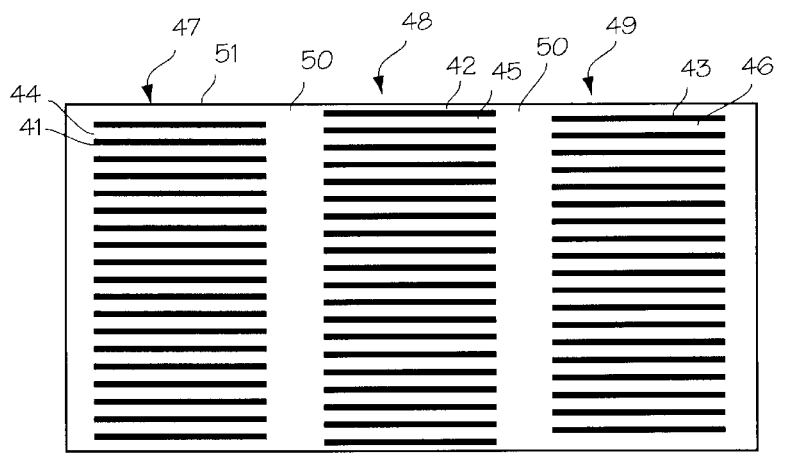
FIG. 9 is a view of a preferred embodiment of the stent.

FIG. 9 shows the stent 1 modified by excision of numerous cutaways 41, 42 and 43 leaving slats or ribs 44, 45, and 46 in eventual outer layer 47, middle layer 48 and inner layer 49. The segments of slats are separated by spines or backbones 50. The slats of each segment are offset so that, when expanded to a roll of approximately three layers, the three layers will overlap to form a barrier between the blood vessel wall and the inner lumen of the expanded stent. The slats shown in FIG. 9 are disposed laterally, aligned in the transverse direction across the width of the stent sheet, parallel to the distal transverse edge 51 or the proximal transverse edge. Of course, where the distal and proximal edges are not straight edges (such a construction may assist attachment to the blood vessel), the slats and cutaways can be described as parallel to the transverse axis of the stent sheet. The stent may be made with at least one, but preferably two layers instead of the three layers used for illustrative purposes herein, or four layers or more, and the number of layers will dictate the spacing of the slats and the cutaways. The slatted construction provides longitudinal flexibility by removing part of the material from the wall of the stent.

Figure 10:
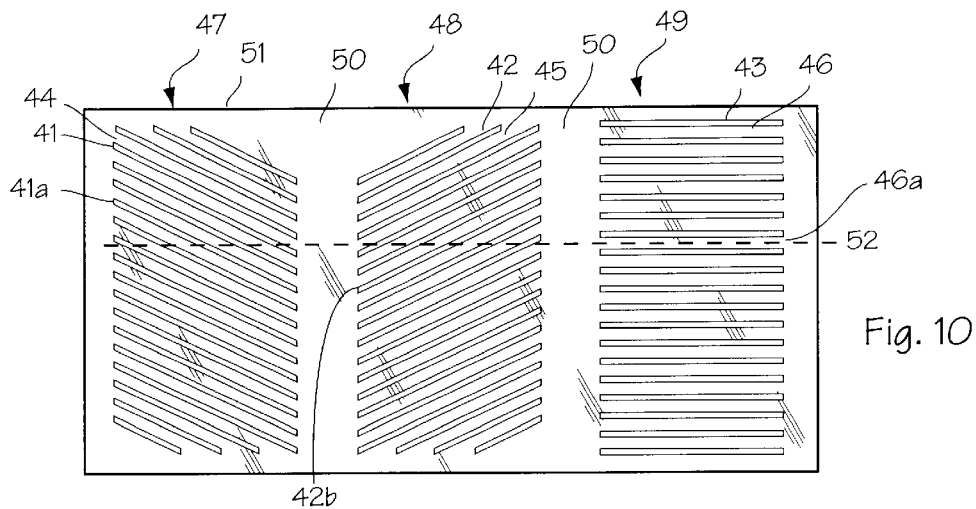
FIG. 10 is a view of a preferred embodiment of the stent.

As shown in FIG. 10, the slats may be disposed at an angle from the transverse direction and still create a barrier between the blood vessel lumen and the outer surface of the stent. In the outer layer section 47 of the stent, the slats are disposed at an angle, shown at angle of about 45° from the transverse direction. The angle of 45° is shown as one of the preferred embodiments but is to be considered merely illustrative of the infinite number of possible arrangements. In the middle layer section 48 of the stent the slats are disposed at an opposing angle, again shown merely for illustration to be about 45° from the transverse direction, but opposite the angle of the slats in the outer layer section. These two layers, when overlapping, will provide a nearly imperforate roll, with passages through the wall of the stent only at the intersections of the cutaways. These passages are, however, blocked by the transversely oriented slats of inner layer section 49. The slats are sized and dimensioned to ensure that, when expanded within the target vessel, the three layers together form a barrier between the outside of the stent and the inside of the stent. Thus if perfect three layer overlap and alignment were expected, each slat could be of equal size and the transverse inner layer slats 46 could be the same width as the passage created by the intersection of the cut-away slots in the other layers. However, to allow for an imperforate wall when the layers are not perfectly aligned and perfectly overlapping in three layers, the inner layer slats 46 are made slightly wider than the corresponding cutaways on the outer and middle layers. The dashed line 52 shown in FIG. 10 illustrates that the center point of cutaway 41*a* and 42*b* will intersect when the stent is rolled in three layers, and that slat 46*a* will correspond to the intersection and block the gap created by the intersection of the two diagonal slots.

Figure 11:
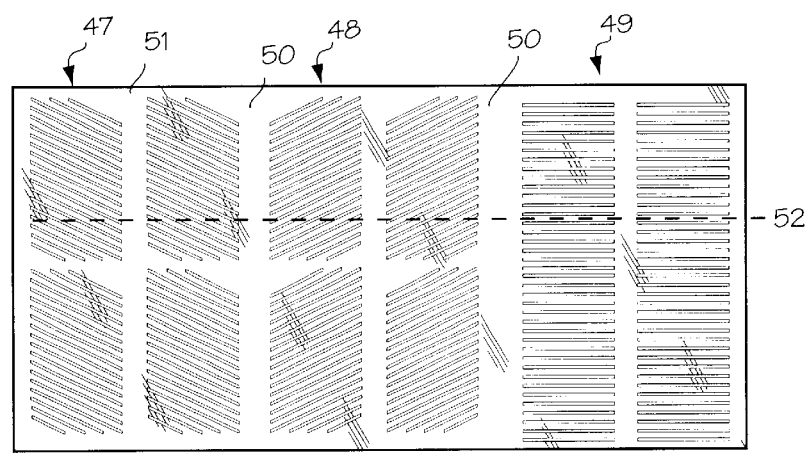
FIG. 11 is a view of a preferred embodiment of the stent.

FIG. 11 shows that numerous patterns of cutaways may be conceived to provide a multi-layered stent wherein each layer contains plurality of slots or perforations, but, when rolled so that the layers are disposed in concentric arrangement, the layers combine to form an imperforate wall. In the outer layer section, the slots are aligned on an angle from the transverse axis, while the slots in the middle layer are arranged at an opposing angle relative to the slots on the outer layer. The numerous slots on the inner layer are arranged so as to correspond to the areas of overlap of the outer and middle layer, leaving the slats to cover the open areas where the slots of the middle and outer layers overlap. Thus, FIG. 11 illustrates that the number and arrangement of slots may be highly variable while still providing an imperforate overall construction with highly perforate walls.

Figure 12:
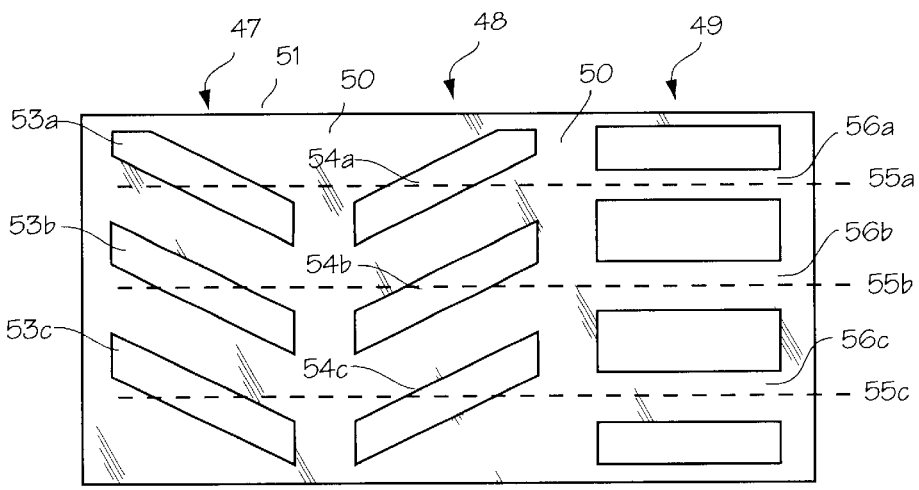
FIG. 12 is a view of an alternative embodiment of the stent.

FIG. 12 is provided as an illustration of the concept. It is more clearly demonstrated in the simple embodiment of FIG. 12 that the cutaways 53*a*, 53*b* and 53*c* on the outer layer and the cutaways 54*a*, 54*b* and 54*c* will, when the outer layer is rolled over the middle layer, intersect along lines 55*a*, 55*b* and 55*c*. The slats 56*a*, 56*b* and 56*c* on the inner layer are intersected by lines 55*a*, 55*b* and 55*c*, and correspond to the expected gap created by the intersection of the diagonal cutaways. The inner section slats may be made larger that the expected gap created by the diagonals to ensure blockage of the gap when the roll is either looser or tighter than exactly three layers, or misaligned. The concept may be applied to any number of layers, the general rule being that the slats of each layer, when rolled over top of each other, form an imperforate wall. Thus, the longitudinal flexibility of the tightly rolled stent is promoted by ribbed or slatted construction (or, alternatively, slotted construction) in which the various layers of the stent are provided with numerous slats which counter align when the stent is expanded to form an imperforate wall from a plurality of perforate layers.

The backbones 50 created between the slatted sections can be arranged so that they are aligned when the stent is tightly rolled, to provide increased flexibility during insertion. The backbones may also be created so that they are aligned when the stent is unrolled and deployed within the blood vessel to provide extra flexibility when unrolled in the install configuration. Careful selection of the tightly rolled size will permit alignment of the backbones during both the tight rolled insertion configuration and the loosely rolled deployed configuration. For example, if the diseased vessel for which the stent is intended is about 2 mm in inner diameter, it will have an inner circumference of about 6.3 mm (2 mm×π). A stent designed for this size vessel may have one or more segments with backbones spaced about 6.3 mm apart, so that when unrolled each segment will cover one entire circumference, and the backbones will all be on one side of the vessel. When rolled tightly to fit within the sheath or upon the distal tip of the catheter (as shown in FIGS. 4 and 5), the stent may be rolled to a diameter of 1 mm or 0.5 mm (or, for example, in relation to the preferred embodiments, any integer fraction ½, ⅓, ¼ . . . of the deployed diameter, and realizing that other relationships will apply to other embodiments), so that the backbones are layered upon each other. Thus all the backbones are disposed on one side of the roll in both the deployed diameter and the tightly wound diameter.

Figures 13, 13A:
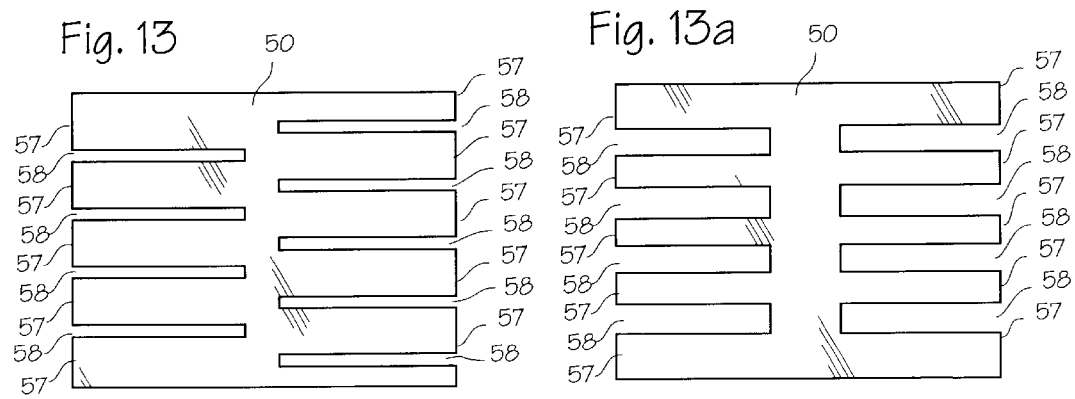
FIG. 13 is a view of an alternative embodiment of the stent.
FIG. 13a is a view of an alternative embodiment of the stent.

FIG. 13 shows another embodiment of the ribbed stent. In this embodiment, a single backbone 50 supports several ribs 57 which are unrestrained at the outer edges of the ribs. The ribs are flat and wide, with gaps 58 on one side of the backbone which are offset from the gaps on the other side of the backbone. When rolled into a tight roll (upon a catheter distal tip or inside a sheath, as illustrated in FIGS. 4 and 5), or unrolled within a blood vessel, the ribs overlap each other and form an imperforate wall. The ribs on one side of the backbone are aligned with the interstitial gaps on the other side of the backbone, thus creating an interfering pattern in much the same manner as described above in relation to FIG. 9. The backbone is the only region of this stent that is continuous from the distal end of the stent to the proximal end of the stent, and this eliminates much of the resistance to longitudinal flexibility and allows the stent to be bent around tight curves in the vasculature without crimping or creasing.

Note that by shifting any segment of slots upward or downward, the rolled stent will have a loosely rolled deployed configuration in which the walls of the stent are perforated. Thus, in reference to FIGS. 9, 10, 11 or 12, the gaps closed by the slats of the third segment as described above may be maintained open by shifting slats upward or downward slightly so that they no longer block the gap. Construction of such a perforate multi-layered stent will allow flexibility of the stent in the undeployed and deployed configuration, provide for perforations allowing vessel ingrowth, better retention of the stent, or ability to pass blood into perforating vessels, yet still provide for the extra resistance to compression afforded by multiple layers.

The slots provided in the wall of the stent may be locally enlarged to create regions of highly perforate wall in the stent. This may be medically indicated when it is desired to maintain patency of the numerous side branches and perforator blood vessels which are supplied with blood by the typical intra-cranial blood vessel. In reference to FIG. 13, the circumferentially extending ribs on either side of the backbone 50 may be aligned so that the ribs on one side overlap the ribs on the other side, thereby creating openings in the wall of the deployed rolled stent which correspond to the open areas 58 between the ribs 57. This configuration is shown in FIG. 13*a*. The stents of FIGS. 9 through 12 may be modified accordingly, providing regions of relatively larger slots which prevent occlusive overlap of the slats, thereby maintaining patency of many side branches and perforating blood vessels fed by the stented blood vessel. This may be achieved with broad backbones and narrow slats of minimal width relative to the slots, so that occlusion is achieved only along the overlapping backbones. It may also be achieved by providing some of the slatted areas of a stent constructed according to FIG. 11 with overlapping and occluding dimensions while providing other slatted areas with dimensions which result in a highly perforate, non-overlapping or completely patent structure in the loosely rolled deployed configuration.

Figure 15:
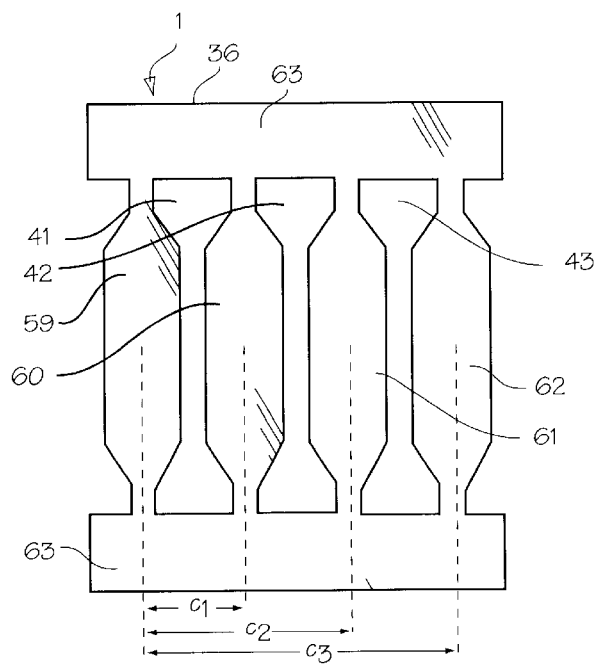
FIG. 15 is a view of an alternative embodiment of the stent with slats running in the longitudinal direction.

Another embodiment of the rolled stent is shown in FIG. 15. This stent is a variation of the slatted stent illustrated above. The slats are aligned longitudinally in relation to the catheter and blood vessel, and perpendicular to the transverse edge or wrap length 36. The slots 41, 42, and 43 are narrow relative to the slats 59, 60, 61 and 62. To create a loosely rolled stent in a substantially imperforate wall from this stent, the wrap length 36 is several times longer than the circumference of the target blood vessel. When the stent is loosely rolled to approximate the inner diameter of the blood vessel lumen, the gaps between longitudinally oriented slats in one layer will be blocked by the slats in other layers. Occlusion of the stent wall will occur for all vessel circumferences which are approximately equal to the distance between the center of one slat and the center of one slot. Thus an imperforate wall is formed from this highly perforate embodiment of the rolled sheet stent for vessels with diameters corresponding to lengths $C_1$, $C_2$, and $C_3$, equivalent to the distance from the reference slat 59 to the center of each of the various slots. The bar-bell shape of the slots (cutaway portions) creates fusiform or tapered shaped slats joined to the end bands 63 provides additional flexibility for the stent when tightly rolled to fit within (or upon) the distal tip of the delivery catheter.

In relation to each of the embodiments described above, the stent may be configured to provide a section (either an arcuate segment or a longitudinal segment, which is substantially imperforate, while the remaining portions of the stent are substantially perforate or open. This allows for occlusion of the aneurysm or target site of disease while permitting flow of blood between the vessel wall and the blood vessel lumen in other areas of the stent. This allows blood flow to any branch blood vessels or perforator blood vessels which supply blood to the brain. The "H" shaped stent of FIG. 21 accomplishes this, and variations on the alignment of the slot patterns on the multi-layered stents of FIGS. 8 through 12 will accomplish such an arrangement.

All of the stent configurations are intended for use while visualized under fluoroscopy. Fluoroscopy will also be used to view the stent during follow-up to ensure continued proper placement. Thus the stent may be coated with radiopaque material such as tantalum to enhance visibility under fluoroscopy. The stent may be coated with a number of substances which help prevent thrombus or coagulation of blood around the stent or in the nearby blood vessel which may be affected by the stent. Paralyne, polyurethane, polyester, polyphosphazene, Dacron, Nylon, silicone, polymers and biopolymers, heparin and albumin coatings, negative ion coatings, tin, and acids such as polylactic acid and polyglycolic acid may be used. Various medications may be bound to the coating, and medications such as heparin, methotrexate, forskolin are contemplated for use. The surface of the stent may also be made microporous with perforations of, for example, about 0.001" diameter to enhance the vessel ingrowth into the stent for better stent/vessel attachment and to improve thrombogenicity.

Figure 16:
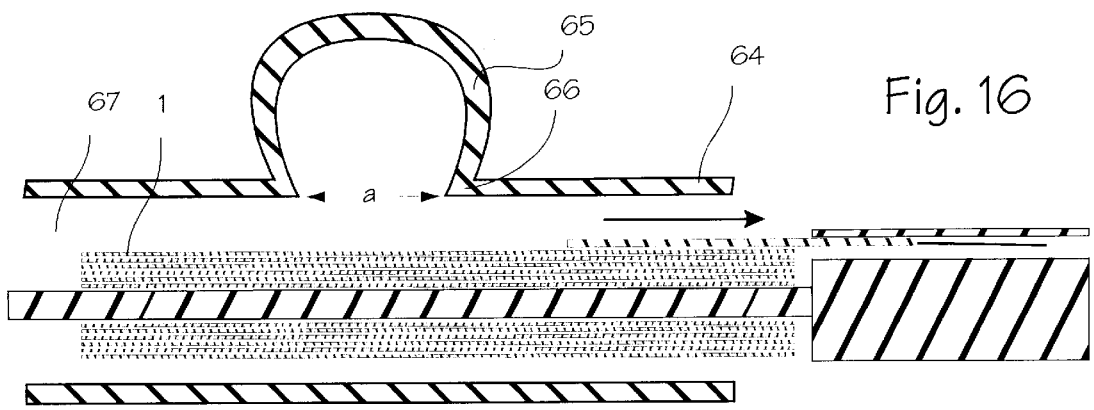
FIG. 16 is a cross section of diseased artery with the stent in place.

The stent is placed with the insertion catheter into an artery within the skull or brain, such as the many arteries pointed out in reference to FIG. 1. The catheter is inserted into a blood vessel of a patient, typically the femoral artery, and the distal tip with the stent mounted thereon is steered into an intra-cranial blood vessel of the patient. In the close-up view of FIG. 16, the stent is shown in an artery exhibiting an aneurysm which could rupture or lead eventually to occlusion, both life threatening events. The blood vessel 64 includes a saccular aneurysm 65. The aneurysm and aneurysm neck may vary in size. Small aneurysms are those of 0–10 mm diameter. Large aneurysms are 10–25 mm in diameter, and giant aneurysms are greater than 25 mm in diameter. Distance a represents the size of the aneurysm neck. In clinical discussion, a wide-neck aneurysm has a neck which exceeds 4 or 5 mm. The stents described herein may be used with aneurysms of all sizes.

Figure 17:
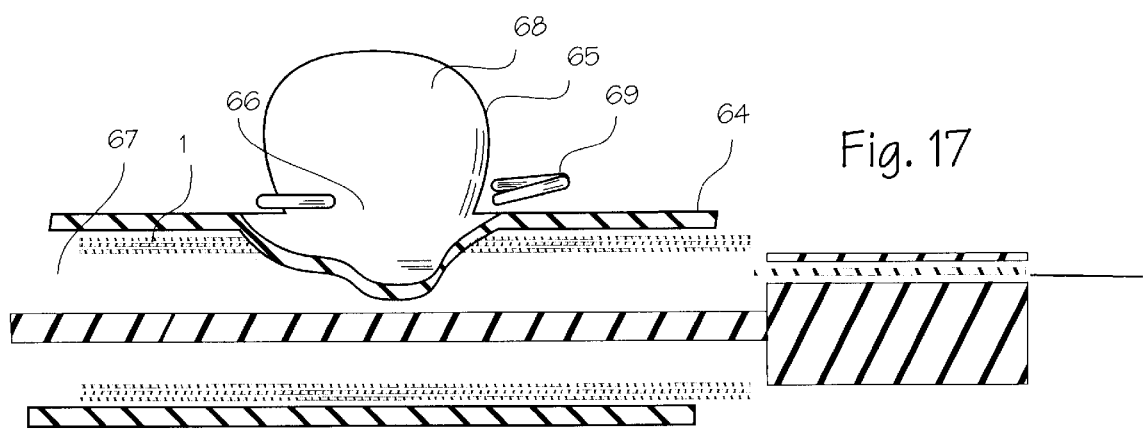
FIG. 17 is a sectional view of a diseased artery with the stent being used in conjunction with aneurysm clips.

The placement of the stent 1 straddles the aneurysm. Once in the diseased portion of the intra-cranial artery, the stent is maneuvered into place in the proximity of the aneurysm, with the stent straddling or bridging the neck 66 of the aneurysm. Once in position, the retaining clip is pulled back into the side lumen thereby releasing the stent within the intra-cranial artery. The solid walled stent, or the modified stent, unrolls to form an imperforate barrier between the arterial wall and the center of the stent, and immediately isolates the sac 65 from the blood vessel lumen 67. This is shown in FIG. 17, in which the stent has unrolled from an original tightly rolled configuration shown in FIG. 16 to a partially unrolled configuration with three layers of stent material.

Upon placement of the stent, the blood flow is redirected from the target opening and the aneurysm is isolated from the high blood pressure of the vascular system, and the threat of hemorrhage is eliminated. In this manner, a patient showing signs of acute distress from a cerebral aneurysm may be treated immediately in a manner that stops or prevents rupture and hemorrhage. Placement of the stent immediately seals off the aneurysm to protect against bleeding or rupture, in contrast to prior art open walled stent placements used in larger peripheral arteries which require significant time for the formation of fibrous tissue within the aneurysm and formation of endothelial cells to create a barrier which isolates the aneurysm from the high pressure of the vascular system. Gradual retraction of the aneurysm or tumor after exclusion and resultant lack of blood flow should relieve any mass effect caused by the size and pressure of the aneurysm or tumor against other structures in the brain.

Figure 18:
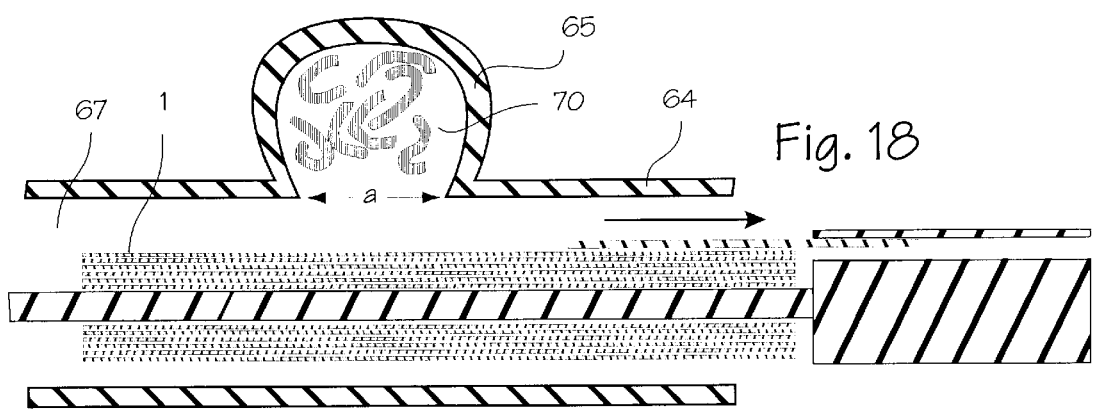
FIG. 18 is a sectional view of a diseased artery with the stent being used in conjunction with detachable coils.

The stent may be left in place as the permanent treatment for the aneurysm or target vessel, or it may be used as a temporary means of re-directing blood flow for stabilizing a patient while considering or actually performing more invasive treatment. Aneurysm clipping, which is one of the standard treatments for intra-cranial aneurysm, is plagued by the risk of rupturing the aneurysmal sac during the surgery. As shown in FIG. 17, the aneurysm may be clipped in accordance with known procedures while the stent is in place. To place the clips, the brain must be exposed and dissected away from the aneurysm so that the clips may be placed at the base of the aneurysm. Rupture during surgery makes the surgery more difficult, decreases visibility and requires additional dissection, contaminates the brain with blood, and makes it more difficult to seal the aneurysm with the clips. With the stent 1 expanded within the blood vessel, the brain is dissected away from the aneurysm to expose the outside 68 of the aneurysm. Clips 69 (shown in FIG. 17) may be placed at the neck of the aneurysm and squeezed closed upon the aneurysm, thereby further sealing the aneurysm sac from the blood vessel. After the aneurysm has been successfully clipped and thereby isolated from the high pressure of the blood vessel, the stent may be removed from the lumen of the blood vessel. FIG. 18 shows that the stent may also be used to immediately isolate the aneurysm after placement of GDC's. Several Guglielmi detachable coils or other such detachable coils 70 are shown inside the aneurysm sac 65. The coils will, in the usual case, eventually cause coagulation and clotting within the aneurysm. However, the patient is at risk during the period required for successful development of the occluding mass caused by the bodies reaction of the coils. To ensure immediate isolation of the aneurysm from the blood vessel, and to ensure that the coils do not escape the aneurysm sac and float downstream to cause embolization or clotting in healthy portions of the blood vessel, the rolled stent is deployed immediately before or after placement of the coils. When used in this manner, the stent is used as an adjunctive to surgery to make it safer and eliminate the complications arising from invasive surgery. In cases where a patient is presented in an emergency condition, perhaps suffering from a ruptured intracranial aneurysm, immediate placement of a solid walled or slightly perforate stent may be the only way to save the patient's life while preparing for other surgery. Placement of coils may be accomplished through the wall of the stent, where the stent is slightly perforate (with a high metal to vessel wall ratio) or where the coils may be pushed into the aneurysm through slots in the wall of an imperforate stent constructed according to FIGS. 9–16.

Figure 19:
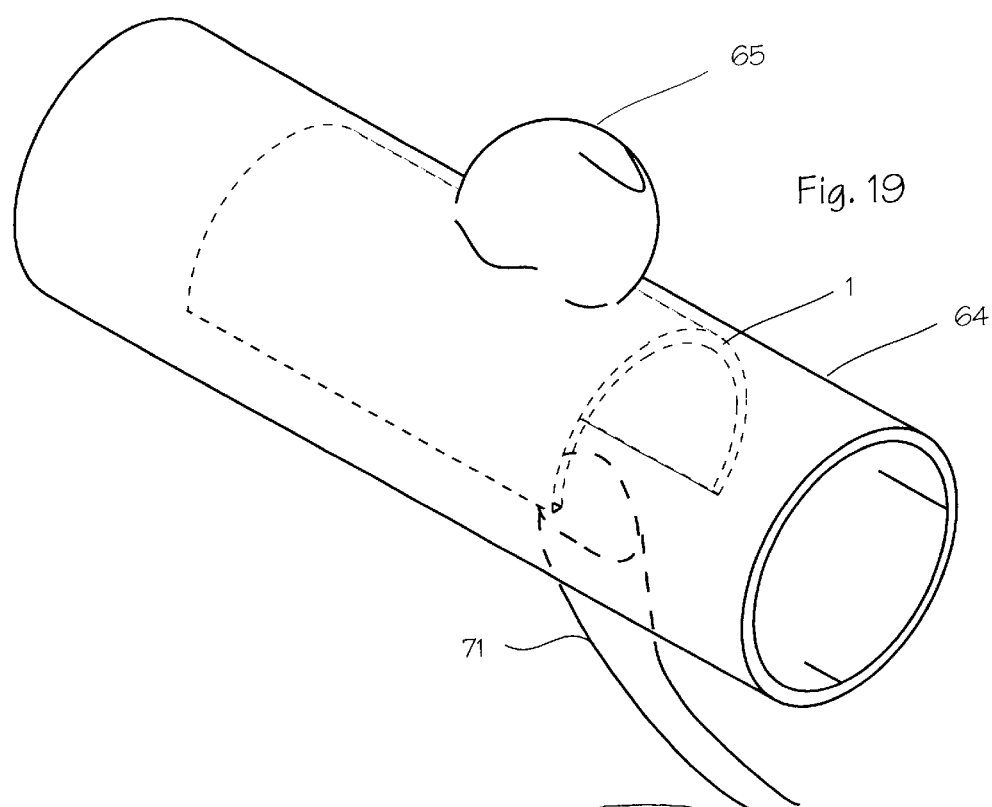
FIG. 19 is a view of an embodiment of the stent in place within a diseased artery.
Figure 20:
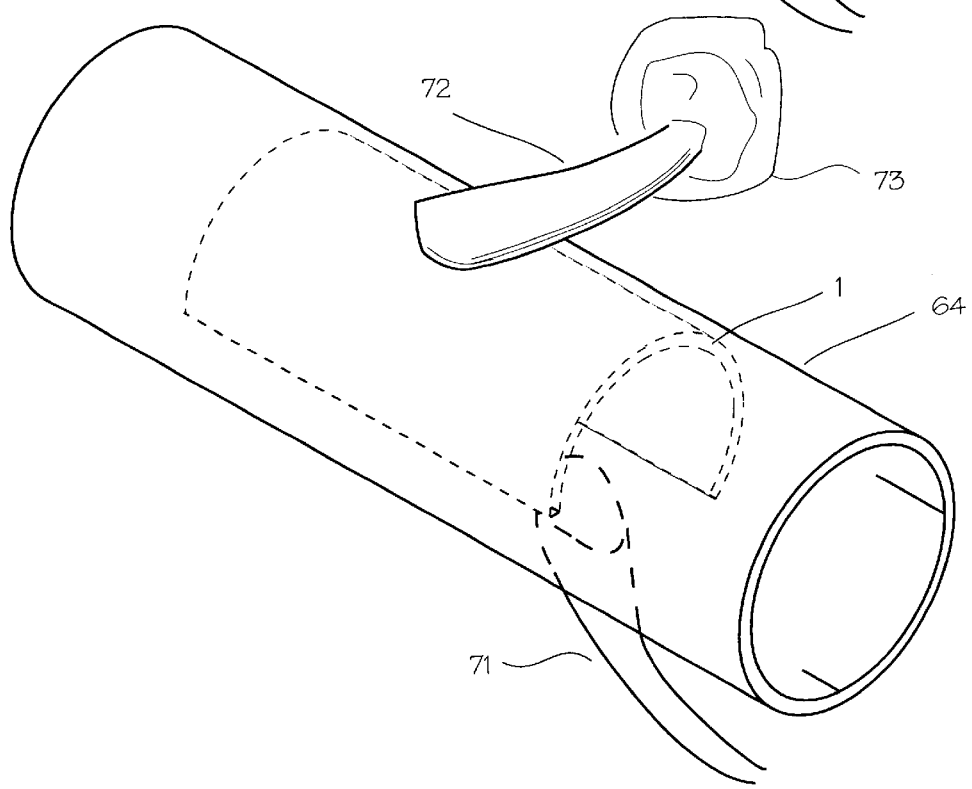
FIG. 20 is a view of an embodiment of the stent in place within a diseased artery.

FIG. 19 illustrates another embodiment of the stent as well as another method of using the stent to isolate an aneurysm 65 from the blood stream. The stent 1 has been inserted into the blood vessel 64 and covers the opening of aneurysmal sac 65. A blood vessel 71 (it may be a branch that is supplied by blood vessel 64 or it may supply blood vessel 50) joins blood vessel 64 near the aneurysm. A rolled stent which unrolls to cover all 360° of the blood vessel inner wall will cover both the aneurysm and the blood vessel 71, but it is usually desirable to maintain flow to or from this blood vessel. In this case, a stent 1 with a short wrap length is used. The stent has a wrap length which is shorter than the internal circumference of the blood vessel, so that when unrolled within the blood vessel it expands to meet the inner wall of the blood vessel but covers less that the entire circumference of the blood vessel wall. The elasticity and spring force of the stent will hold it in position against the blood vessel wall and isolate the aneurysm from the blood vessel. FIG. 20 illustrates another situation where the resilient half stent is used. The blood vessel and branch blood vessel are normal and healthy. Another branch vessel 72 supplies blood from the main blood vessel 64 to a diseased area 73. The diseased area may be an aneurysm or fistula in the branch blood vessel, a tumor supplied by the branch blood vessel, or any other vascular disease. The half stent has been released within the main blood vessel 64 so that it blocks blood flow to the branch blood vessel, thereby isolating the diseased area from the blood stream. The diseased area will necrose and be absorbed by the body over time, thereby alleviating the condition without surgery directly in the area of the disease.

When used in this manner in a perfectly round blood vessel, the stent must have a wrap length of at least half the inner circumference of the blood vessel so that it covers at least 180° of the inner wall of the blood vessel. However, in a real blood vessel which is not perfectly round, it may be sufficient that the wrap length be about half the inner circumference of the blood vessel, and cover about 180° of the inner wall, and coverage of at least 180° will be useful in a wide range of blood vessels. In use, it will be most practical to select a wrap length which results in about 210° to 270° of coverage (with wrap length corresponding to about ¾ of the expected inner wall circumference), to ensure a good fit, adequate resilience for expansion and holding power, and sufficient clearance for the branch blood vessel.

The half layer stent shown in FIGS. 19 and 20 may be provided as a single imperforate sheet, or it may include any pattern of slots as illustrated in FIGS. 6–9. The half layer stent should be mounted on the catheter distal tip (FIG. 4) or within the catheter sheath (FIG. 5) so that it is properly aligned with the side branch or aneurysm to be blocked. The retaining clip made of tantalum or a tantalum marker on the sheath will provide the reference point for the surgeon during placement, so that rotational and longitudinal alignment with these markers will allow proper release and placement of the stent. The rolled stent may be centered under the retaining clip so that the clip corresponding to the side of the vessel where the stent is to be placed.

Figure 21:
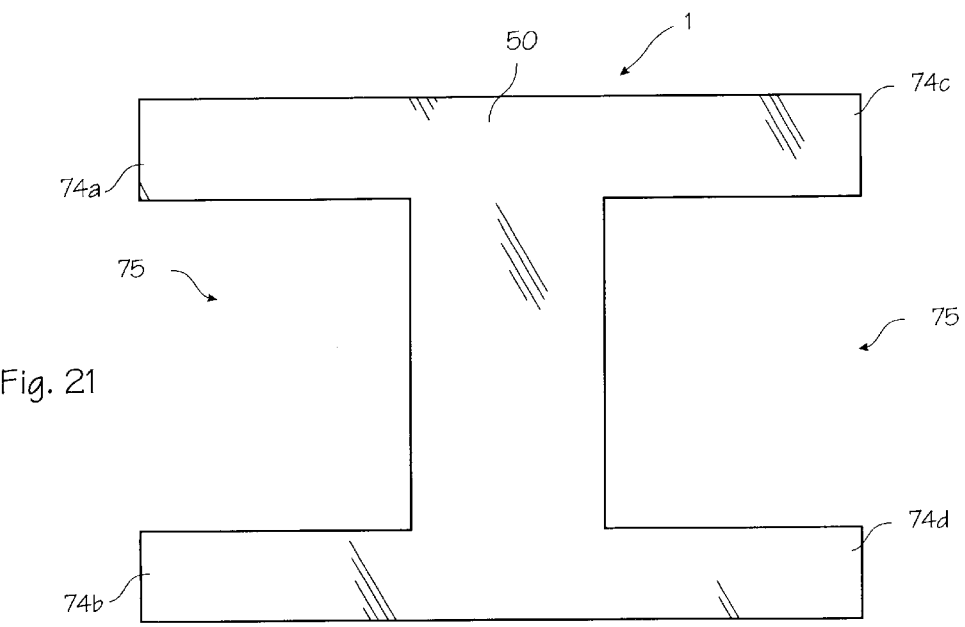
FIG. 21 shows and alternative embodiment of the stent.

FIG. 21 shows another variation of the stent. This stent is shaped like the letter "I" or the letter "H." The backbone 50 is augmented with integrally formed ribs or tabs 74a, 74b, 74c and 74d extending transversely from the backbone at the distal and proximal ends of the stents. The transversely extending tabs create open areas 75 The transverse edge preferably exceeds the circumference of the blood vessel in which the stent is inserted. The single backbone will provide the occluding surface area of the stent, while the ribs serve to provide radial expansive strength for the stent to provide stronger deployment and holding resilience.

Figure 22:
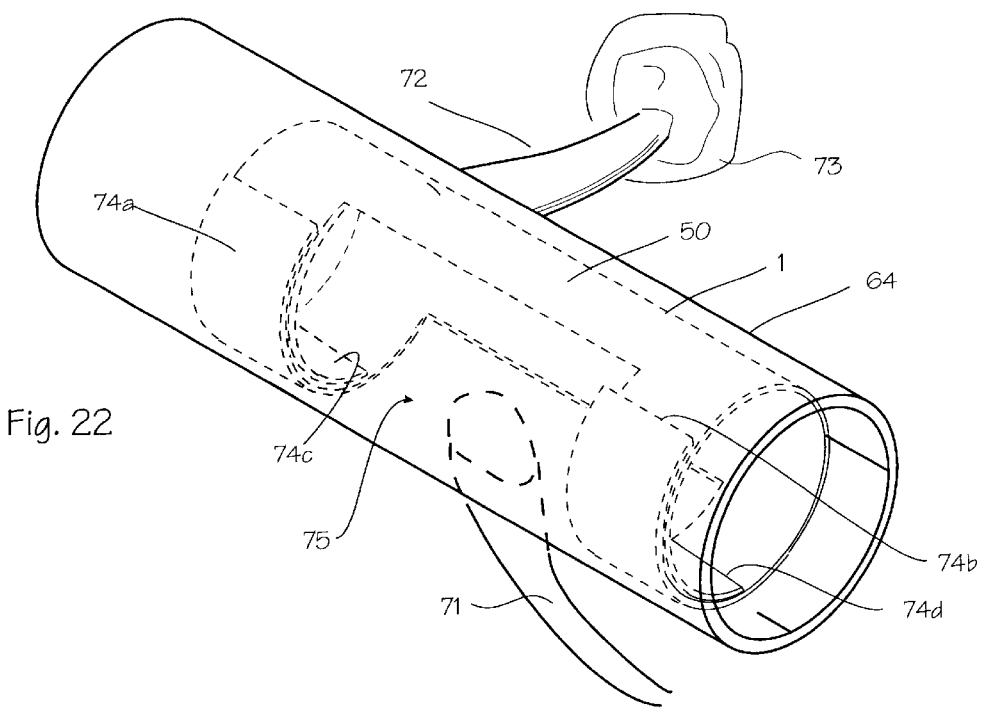
FIG. 22 is a view of an embodiment of the stent in place within a diseased artery.

As shown in FIG. 22, the loosely rolled deployed configuration of the stent has the backbone 50 occluding the target vessel 72, while the ribs or tabs extend circumferentially over the entire circumference of the blood vessel to hold the stent in place. The ribs may overlap somewhat, as shown, creating an arcuate open space 75 in what would otherwise be the wall of the stent. Branch blood vessel 71 is not occluded because the stent is placed so that the cutaway portions of the stent overlie the opening into the blood vessel 64. Thus, in use, the stent provided with an occluding sheet with transversely extending retaining bands on the distal and proximal ends is placed within the blood vessel so that the occluding sheet occludes a diseased branch vessel, aneurysm or other AVM while circumferential portions of the blood vessel opposing the occluding diseased branch vessel, aneurysm or other AVM are not covered by the occluding sheet, thereby allowing blood flow between the blood vessel and any branch blood vessel communicating with the blood vessel at a site opposite the occluding sheet.

Figure 23:
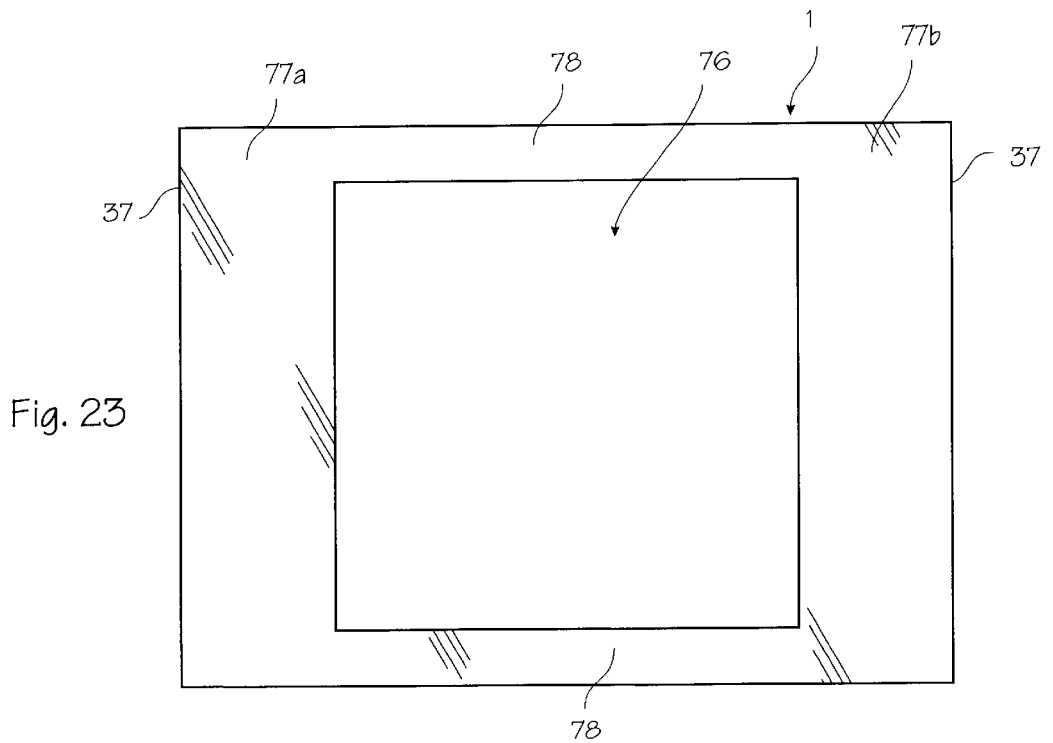
FIG. 23 shows an alternative embodiment of the stent.
Figure 24:
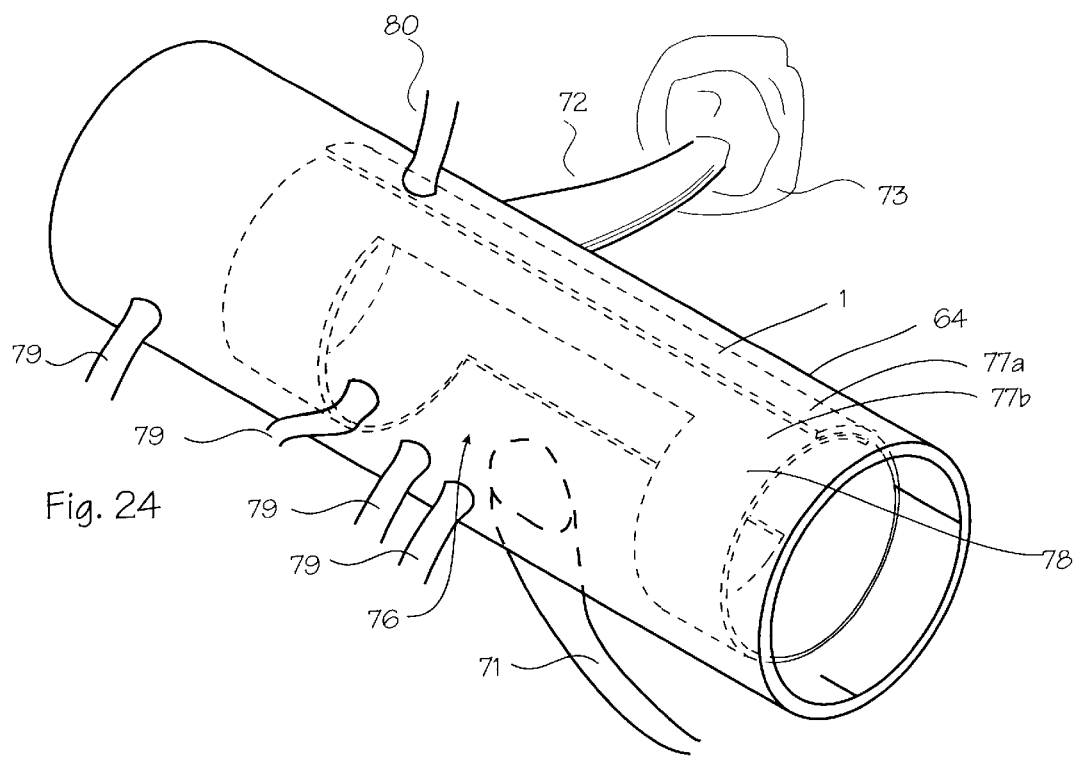
FIG. 24 shows an alternative embodiment of the stent in place within a diseased artery

FIGS. 23 and 24 illustrate another embodiment of the rolled sheet stent. This stent takes the shape of an open frame with an open central area 76. Side-frame pieces 77a and 77b will provide the occluding surface for this stent, and distal end and proximal end pieces 78 will provide radial support for the stent. When rolled within a blood vessel as shown in FIG. 24, the overlapping side frame pieces occlude the diseased branch vessel, aneurysm or other AVM designated generally at item 73. As with the stent of FIG. 21, this stent is placed within the blood vessel so that the open portion overlies the healthy branch vessel 71 while the occluding sheet made up in this instance of side frame pieces covers the diseased blood vessel 72. In FIG. 24, several perforator vessels 79 are shown to illustrate that there will typically be several perforators left open and un-occluded by the open area of the stent, while other perforators, such as perforator 80, may be occluded by the stent. In the deployed configuration, the stents of FIGS. 22 and 24 will appear to be very similar, comprising an arcuate occluded segments and an arcuate un-occluded segments. The occluded segment is created by the spine 50 in FIG. 22 or side pieces 77a and 77b in FIG. 24, and the un-occluded segment is created by the central opening 75 or 76.

Catheter placement may be facilitated with the use of common guide catheters and guide wires. Expansion of the stent may be aided by a micro-balloon placed at the tip of the insertion catheter. Other features described, such as the materials of the stent, the arrangement, number and degree of openings or slats, and geometry of the release tab may be improved upon as experience with the devices and methods described above dictates. Thus, while the preferred embodiments of the devices and methods have been described, they are merely illustrative of the principles of the invention. Other embodiments and configurations may be devised without departing from the spirit of the inventions and the scope of the appended claims.

We claim:

1. A stent delivery catheter for use within a blood vessel of the brain, said system comprising:

a catheter having a distal and a proximal end, said distal end comprising a sheath, said distal delivery sheath having an inner diameter;

a stent disposed within the sheath, said stent characterized an inner diameter;

a push rod disposed within the distal delivery sheath, proximal to the stent, said push rod having a distal face and said distal face of the push rod having a diameter closely matching the inner diameter of the distal delivery sheath;

wherein the distal face of the push rod is characterized by an outer diameter, and a beveled rim is disposed around the outer diameter, and the beveled rim extends distally from the distal face.

2. The stent catheter system of claim 1 further comprising:

a lumen disposed within the push rod, said central lumen defining a central rim on the distal face of the pushrod;

a retainer disposed distal to the stent, said retainer having a receiving bore with an inner diameter closely matching the outer diameter of the stent;

a retainer control rod extending longitudinally through the lumen of the push rod, and through the stent, the retainer control rod having a distal end connected to the retainer, wherein the retainer control rod is operable from a proximal end of the stent to push the retainer distally relative to the stent.

3. The stent catheter system of claim 2 wherein the retainer control rod includes a segment with an outer diameter substantially smaller than the inner diameter of the stent.

4. The stent catheter system of claim 2 wherein said central rim is provided with a beveled rim extending distally from the distal face of the push rod.

* * * * *